(12) United States Patent
Fredette et al.

(10) Patent No.: US 7,069,775 B2
(45) Date of Patent: Jul. 4, 2006

(54) BOREHOLE CALIPER TOOL USING ULTRASONIC TRANSDUCER

(75) Inventors: Mark A. Fredette, Houston, TX (US); Scott Ritter, Missouri City, TX (US); Wade D. DuPree, Richmond, TX (US); Miguel F. Pabon, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 155 days.

(21) Appl. No.: 10/711,716

(22) Filed: Sep. 30, 2004

(65) Prior Publication Data

US 2006/0070433 A1    Apr. 6, 2006

(51) Int. Cl.
*E21B 47/10* (2006.01)

(52) U.S. Cl. .................. 73/152.18; 73/152.17
(58) Field of Classification Search .......... 73/152.18, 73/152.17, 152.01
See application file for complete search history.

(56) References Cited

U.S. PATENT DOCUMENTS

| | | | |
|---|---|---|---|
| 2,639,512 A | 5/1953 | Legrand | |
| 2,771,686 A | 11/1956 | Hamontre et al. | |
| 3,023,508 A | 3/1962 | Saurenman | |
| 3,060,588 A | 10/1962 | Lanmon, II et al. | |
| 3,097,433 A * | 7/1963 | Cubberly | 33/544.3 |
| 3,349,498 A | 10/1967 | Oliver et al. | |
| 3,599,085 A * | 8/1971 | Semmelink | 324/386 |
| 3,685,158 A | 8/1972 | Planche | |
| RE28,264 E * | 12/1974 | Semmelink | 324/353 |
| 3,890,502 A * | 6/1975 | Dowling et al. | 250/267 |
| 3,900,826 A * | 8/1975 | Dowling et al. | 367/31 |
| 4,083,237 A | 4/1978 | Levesque | |
| 4,251,773 A | 2/1981 | Cailliau et al. | |
| 4,251,921 A | 2/1981 | Fink | |
| 4,407,157 A | 10/1983 | Lichtenberg | |
| 4,432,143 A | 2/1984 | Moriarty et al. | |
| 4,480,186 A | 10/1984 | Wolk | |
| 4,673,890 A | 6/1987 | Copland et al. | |
| 4,914,826 A | 4/1990 | Nold, III | |
| 4,926,937 A | 5/1990 | Hademenos | |
| 4,979,585 A | 12/1990 | Chesnutt | |
| 5,086,645 A | 2/1992 | Deaton | |
| 5,299,359 A | 4/1994 | Estes et al. | |
| 5,531,112 A | 7/1996 | Young et al. | |
| 5,631,413 A * | 5/1997 | Young et al. | 73/152.29 |
| 6,230,557 B1 * | 5/2001 | Ciglenec et al. | 73/152.01 |
| 6,339,886 B1 | 1/2002 | Reinhart | |
| 6,560,889 B1 | 5/2003 | Lechen | |
| 6,588,542 B1 | 7/2003 | Nakajima et al. | |
| 6,647,637 B1 | 11/2003 | Lechen | |
| 6,702,010 B1 | 3/2004 | Yuratich et al. | |

* cited by examiner

*Primary Examiner*—Hezron Williams
*Assistant Examiner*—Rodney Frank
(74) *Attorney, Agent, or Firm*—Victor H. Segura; Brigitte L. Echols

(57) ABSTRACT

A borehole caliper tool includes a tool body, a bow spring flexibly coupled to the tool body, a target coupled to the bow spring, and an ultrasonic transducer coupled to the tool body, wherein in operation the ultrasonic transducer transmits an acoustic pulse to the target and receives an echo of the acoustic pulse from the target.

21 Claims, 9 Drawing Sheets

BOREHOLE CALIPER TOOL USING ULTRASONIC TRANSDUCER

FIELD OF INVENTION

The invention relates to tools for obtaining subsurface measurements. More specifically, the invention relates to techniques for determining the dimensions of a borehole.

BACKGROUND OF INVENTION

Various caliper tools for gauging the diameter of a borehole are known in the art. In one example, a caliper tool includes one or more bow springs coupled to a tool body. When the tool body is disposed in a borehole, the bow spring engages the borehole wall and expands and contracts as the tool body traverses the borehole and the borehole diameter changes. The motion of the bow spring can provide an indication of the borehole diameter. In this case, a sensing device can be attached to the bow spring and used to monitor the motion of the bow spring. This is taught, for example, in U.S. Pat. No. 2,639,512. Some caliper tools further include one or more rigid arms coupled between the tool body and the bow spring. The rigid arm deflects as the bow spring expands and contracts, and the motion of the rigid arm provides an indication of the borehole diameter.

An electronic sensing device having a movable part is usually used to monitor the motion of the rigid arm. Typical examples of these electronic sensing devices include linear variable differential transformer (LVDT) and potentiometer sensors. An LVDT sensor includes a ferromagnetic core disposed within a series of inductors and produces electrical output proportional to the physical position of the ferromagnetic core within the series of inductors. A potentiometer sensor includes a slider attached to a resistor and produces electrical output proportional to the contact position of the slider on the resistor. The caliper tool uses a mechanical linkage to couple the movable part of the sensing device to the rigid arm so that the electrical output generated by the sensing device is representative of the motion, or deflection, of the rigid arm.

The mechanical linkage is required to satisfy various requirements. For example, the mechanical linkage is required to fit in a small space on the tool body and work in the hydrostatic pressure of the borehole, which frequently exceeds 20,000 psi (138 MPa), and in the presence of drilling mud, which typically contains debris. The mechanical linkage must be mechanically tight to avoid introducing errors in translating the position of the rigid arm to the sensing device. To allow attachment to the mechanical linkage, the movable part of the sensing device would either have to be exposed to borehole pressure and drilling fluid or be located in a compensator filled with oil at borehole pressure.

As evident from conventional configurations, physically linking the sensing device to a rigid arm complicates the design and operation of a caliper tool. A caliper tool that does not require a mechanical linkage to directly translate motion of an arm to a sensing device is desired.

SUMMARY OF INVENTION

In one aspect, the invention relates to a borehole caliper tool which comprises a tool body, a bow spring flexibly coupled to the tool body, a target coupled to the bow spring, and an ultrasonic transducer coupled to the tool body, wherein in operation the ultrasonic transducer transmits an acoustic pulse to the target and receives an echo of the acoustic pulse from the target.

In one aspect, the invention relates to a borehole caliper tool which comprises a tool body; a bow spring disposed on the tool body; an ultrasonic transducer coupled to the bow spring; and an ultrasonic transducer coupled to the tool body, wherein in operation an acoustic pulse is transmitted from one of said ultrasonic transducers for receipt by the other ultrasonic transducer.

In another aspect, the invention relates to a method for gauging a diameter of a borehole, comprising deploying a borehole caliper tool in the borehole, the borehole caliper tool comprising a tool body, a bow spring flexibly coupled to the tool body, a target coupled to the bow spring, and an ultrasonic transducer coupled to the tool body, the borehole caliper tool being deployed such that the bow spring engages with a surface of the borehole; and generating an acoustic pulse using the ultrasonic transducer; receiving an echo of the acoustic pulse from the target; determining a time elapsed between generating the acoustic pulse and receiving the echo of the acoustic pulse; and relating the time elapsed to the diameter of the borehole.

In another aspect, the invention relates to a method for gauging a diameter of a borehole, comprising deploying a borehole caliper tool in the borehole, the borehole caliper tool comprising a tool body, a bow spring flexibly coupled to the tool body, an ultrasonic transducer coupled to the bow spring, and an ultrasonic transducer coupled to the tool body, the borehole caliper tool being deployed such that the bow spring engages with a surface of the borehole; and generating an acoustic pulse using the ultrasonic transducer coupled to the tool body; receiving the acoustic pulse using the ultrasonic transducer coupled to the bow spring; determining a time elapsed between generating the acoustic pulse and receiving the acoustic pulse; and relating the time elapsed to the diameter of the borehole.

In another aspect, the invention relates to a method for gauging a diameter of a borehole, comprising deploying a borehole caliper tool in the borehole, the borehole caliper tool comprising a tool body, a bow spring flexibly coupled to the tool body, an ultrasonic transducer coupled to the bow spring, and an ultrasonic transducer coupled to the tool body, the borehole caliper tool being deployed such that the bow spring engages with a surface of the borehole; and generating an acoustic pulse using the ultrasonic transducer coupled to the tool bow spring; receiving the acoustic pulse using the ultrasonic transducer coupled to the tool body; determining a time elapsed between generating the acoustic pulse and receiving the acoustic pulse; and relating the time elapsed to the diameter of the borehole.

Other features and advantages of the invention will be apparent from the following description and the appended claims.

DETAILED DESCRIPTION OF EMBODIMENTS

In the following description, numerous specific details are set forth in order to provide a thorough understanding of the invention. However, it will be apparent to one skilled in the art that the invention may be practiced without some or all of these specific details. In other instances, well-known features and/or process steps have not been described in great detail in order to avoid obscuring the invention.

Figure 1:
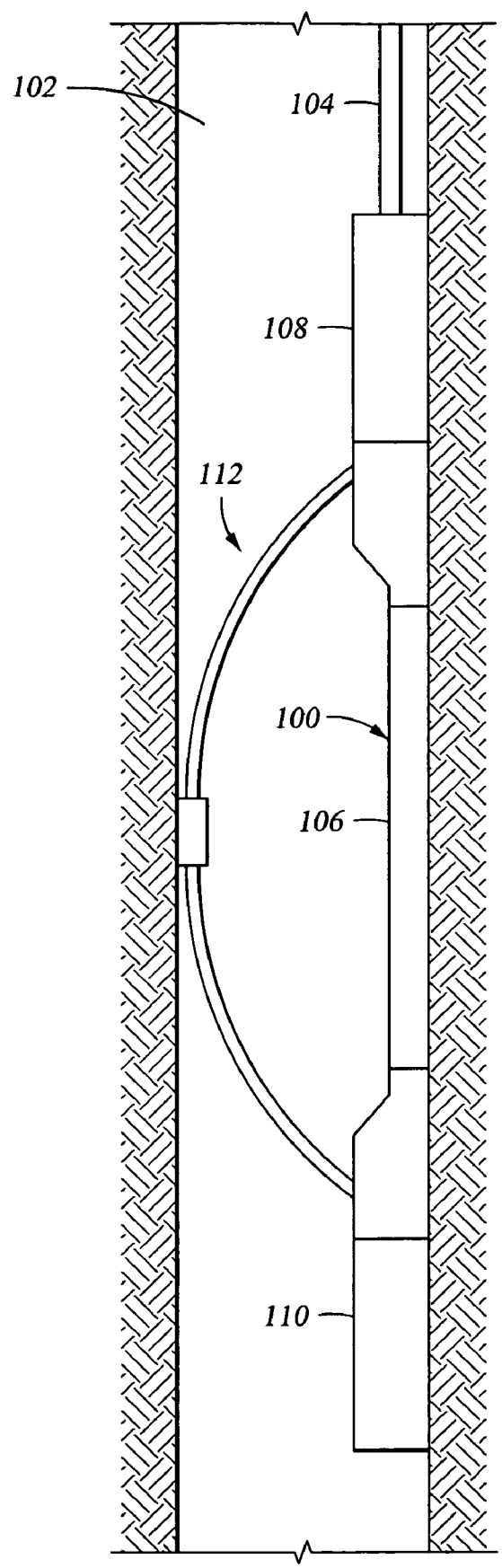
FIG. 1 shows a caliper tool according to one embodiment of the invention in a borehole.

FIG. 1 shows a caliper tool 100 according to an embodiment of the invention. The caliper tool 100 is deployed in a borehole 102. Typically, the borehole 102 will be filled with drilling fluid. The caliper tool 100 can measure and log the diameter of the borehole 102 as it traverses the borehole. The caliper tool 100 could be deployed alone in the borehole 102 on the end of a logging cable 104. Alternatively, the caliper tool 100 could be deployed with a downhole tool (not shown) that performs downhole operations in the borehole 102. The caliper tool 100 includes an elongated tool body 106 attached between an upper body 108 and a lower body 110. The upper body 108 and/or the lower body 110 may include the circuitry needed to record caliper tool measurements and transmit the measurements to the surface. The tool body 106 carries an arm assembly 112. In this embodiment, the arm assembly 112 and the tool body 106 engage or contact the borehole wall while the caliper tool 100 is used to measure and log the diameter of the borehole 102. The arm assembly 112 expands and contracts in response to the changing diameter of the borehole 102. The motion of the arm assembly 112 is tracked to determine the diameter of the borehole 102.

Figure 2:
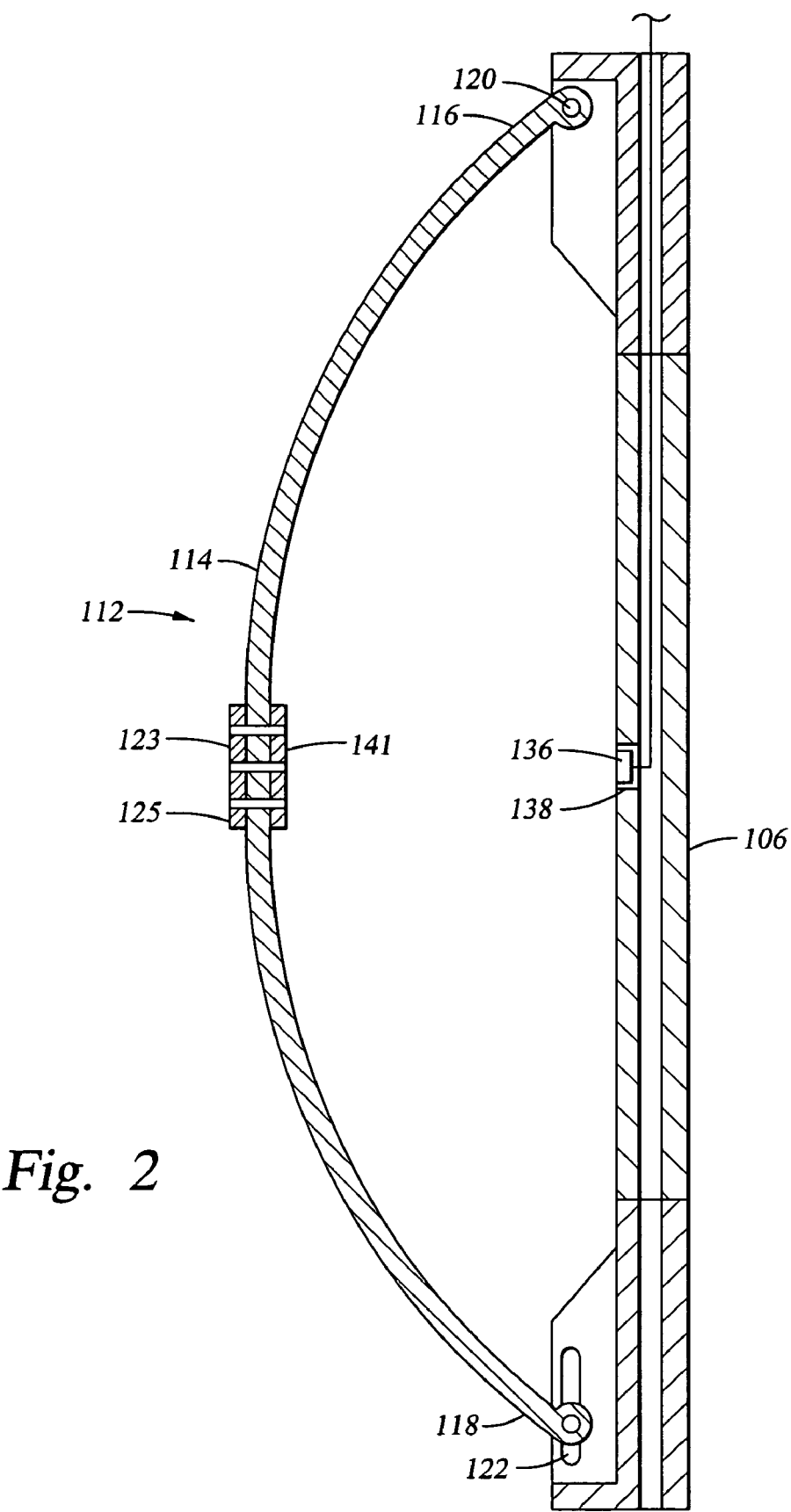
FIG. 2 shows a cross-section of a caliper tool according to one embodiment of the invention.

FIG. 2 shows a cross-sectional view of the tool body 106 and the arm assembly 112 according to one embodiment of the invention. In this embodiment, the arm assembly 112 includes a bow spring 114 having ends 116, 118 coupled to the tool body 106 by joints 120, 122, respectively. The invention is not limited by how the joints 120, 122 are implemented, but the joints preferably allows pivoting of the bow spring ends 116, 118 relative to the tool body 106. In the illustrated embodiment, the joint 120 is shown as a pin-in-hole joint, while the joint 116 is shown as a pin-in-slot joint. Both the (pin-in-hole) joint 120 and the (pin-in-slot) joint 116 allow pivoting of the bow spring ends 116, 118. In addition, the (pin-in-slot) joint 122 allows sliding of the bow spring end 118 along the tool body 106. Thus, the bow spring 114 can expand and contract as the tool body 106 and arm assembly 112 traverse a borehole. A pad 123 is attached to a middle section of the bow spring 114. The pad 123 has a surface 125 for engaging a borehole wall and a surface 141 for reflecting the ultrasonic wave.

An ultrasonic transducer 136 located in a cavity 138 in the tool body 106 is used to track the motion of the arm assembly 112. The ultrasonic transducer 136 generates acoustic pulses, which are transmitted to a target, and then echoed back from the target. The ultrasonic transducer 136 converts the echoes received from the target into electrical signals that are representative of the time elapsed between generation of the acoustic pulses and receipt of the echoes. Electronic circuitry for controlling the ultrasonic transducer 136 and receiving signals from the ultrasonic transducer 136 may be located in the upper body (108 in FIG. 1) or the lower body (110 in FIG. 1) or in the tool body 106. The transmitting and receiving functions of the ultrasonic transducer 136 may be performed by one sensor element or two sensor elements. An example of an ultrasonic transducer suitable for use in the invention is disclosed in U.S. Pat. No. 5,130,950. However, the invention is not limited to this particular ultrasonic transducer. Any ultrasonic transducer that can transmit and receive acoustic pulses in a borehole environment may be used.

Figure 9:
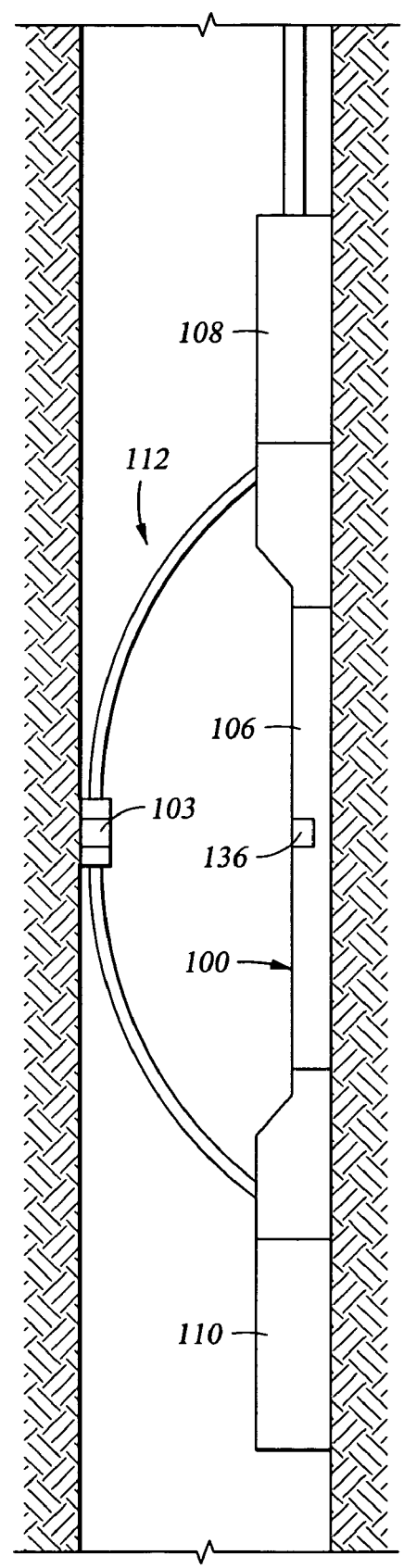
FIG. 9 shows another caliper tool according to one embodiment of the invention in a borehole.

Some embodiments of the invention may be implemented to perform pulse-echo type measurements, where the transducer on the tool body is energized to emit acoustic energy in the borehole fluid such that an acoustic wave travels to a target to be reflected. The transducer is adapted to receive the reflected wave. Other embodiments may be implemented in a "pitch-catch" arrangement. In the pitch-catch arrangement, a receiver 103 replaces the target (See FIG. 9). The receiver 103 may be disposed on the arm with the wiring running through the arm 112 (not shown). Alternatively, the receiver 103 transducer may be adapted to operate as the transmitter and transducer 136 adapted to operate as the receiver. Benefits of pitch-catch configurations include: reducing the path the wave must travel from a round-trip to a one-way and having a dedicated sensor as a receiver; halving the distance traveled results in less attenuation of the signal resulting in a larger received signal which is easier to analyze; and having a dedicated sensor reduces difficulty in discriminating the reflected signal from oscillations (ringing) that may occur in a pulse-echo sensor from the pulse.

Figure 3:
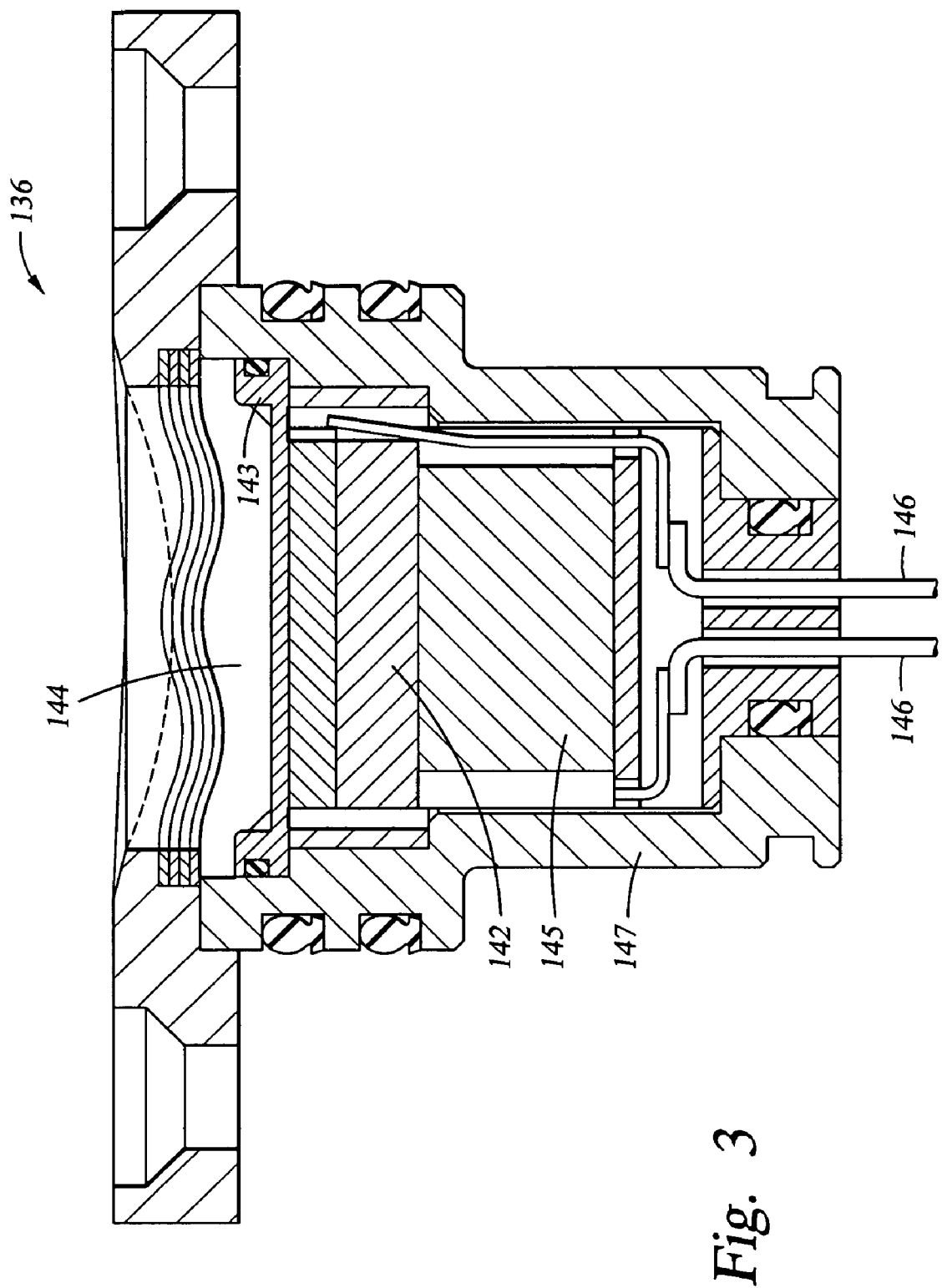
FIG. 3 shows a transducer configuration in accord with an embodiment of the invention.

FIG. 3 shows the cross section of a transducer 136 that may be used to implement the invention in either a pulse-echo or pitch-catch embodiment. The transducer 136 can be mounted in the tool body 106 as shown in FIG. 2 or in any suitable manner as known on the art. A piezoelectric ceramic disk 142 acts alternatively as the signal source and receiver. An inner window 143 made of PEEK™ seals the disk from well fluids. An outer window 144, also made of PEEK™, protects the transducer from physical damage. The stacked windows 143, 144 match the acoustic impedance of the disk 142 to that of the well fluid to optimize energy transfer and minimize internal reflections. A backing 145 damps the oscillations after the transducer excitation is removed. In one embodiment, the backing 145 may be made of rubber loaded with heavy particles such as tungsten carbide. Metal pins 146 connect the disk 142 to the transmitter and receiver electronics (See 108 in FIG. 1). The transducer body 147, preferably made of stainless steel, contains all the pieces and seals against the tool body 106. As known in the art, elements within the transducer 136 may be set at wellbore pressure and vacuum filled with a suitable material. The catch transducer in a pitch-catch embodiment of the invention would not require a large backing 145 and could be sealed in rubber to eliminate the body 147. The dimensions of the transducer 136 may be chosen to balance the overall size against the measurement parameters. The sensor may be operated at any suitable frequency depending on the subsurface conditions as known in the art.

In one embodiment, the surface 141 of pad 123 attached to the bow spring 114 acts as a target for the acoustic pulses generated by the ultrasonic transducer 136. The surface 141 provides a high contrast to fluids in the borehole, thereby reflecting a clear signal and extending the measurement range of the ultrasonic transducer 136. The pad surface 141 may be formed of a metal such as stainless steel. The acoustic impedance of steel (47,000,000 Rayle) is much larger than that of typical borehole fluids (in the neighborhood of 1,500,000 Rayle), so nearly all the incoming acoustic energy is reflected back to the source. In conventional caliper applications of ultrasonics, the reflector is the borehole wall itself, which has a reduced impedance contrast (7,700,000 Rayle for sandstone and shale) and whose rugosity can significantly diminish the amount of energy reflected. Thus in a comparison between steel to perfect rock, steel reflects almost 40% more energy. Seldom is the borehole perfect rock. The sensing end of the ultrasonic transducer 136 preferably faces the surface 141 such that acoustic pulses travel in a generally perpendicular direction between the sensing end of the transducer 136 and the surface 141. Because the pad 123, and therefore the surface 141, moves relative to the ultrasonic transducer 136 during measurements, a surface 141 large enough to receive acoustic pulses from the ultrasonic transducer 136 during movement is preferable.

In this embodiment, the ultrasonic transducer 136 measures the travel time of an acoustic pulse transmitted from the ultrasonic transducer 136 to the surface 141 and echoed back to the transducer 136. From the travel time measured by the transducer 136, the distance from the transducer to the surface 141 can be determined using the sonic velocity of the fluid in the borehole. The borehole diameter, D, may be expressed as follows:

$$D = d_{pu} + d_{ut} + d_{pd} = \frac{vT}{2} + d_{ut} + d_{pd} \quad (1)$$

Figure 4:
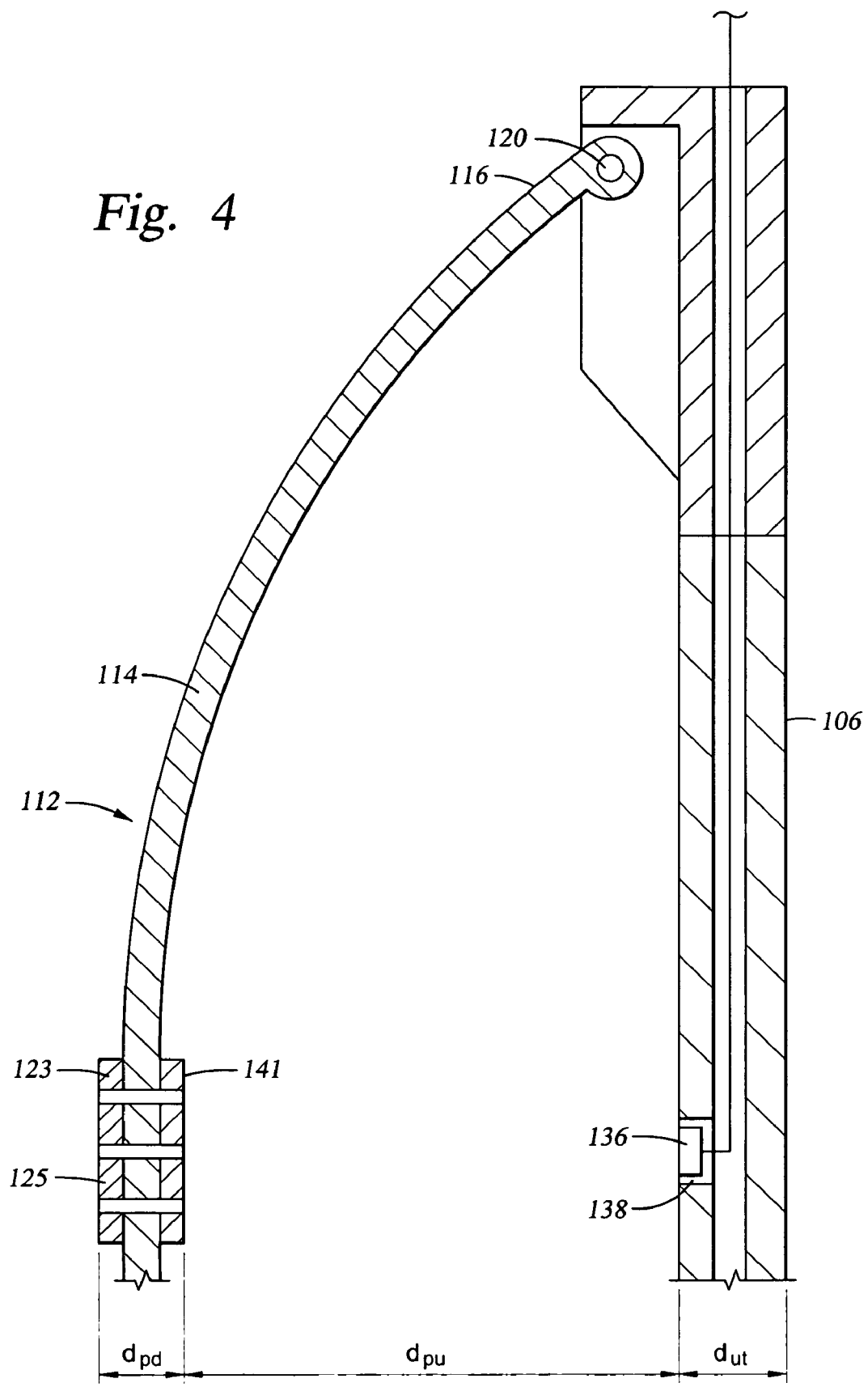
FIG. 4 is a schematic diagram illustrating certain operation principles of the caliper tool of FIG. 2.

As illustrated in FIG. 4, $d_{pu}$ is the distance from the surface 141 to the ultrasonic transducer 136, $d_{ut}$ is the distance from the ultrasonic transducer 136 to the edge of the tool body 106 (in contact with the borehole wall), $d_{pd}$ is the distance from the surface 141 to the pad surface 125 (in contact with the borehole wall), v is the sonic velocity of the drilling fluid, and T is the travel time of an acoustic pulse from the ultrasonic transducer 136 to the surface 141 and back to the ultrasonic transducer 136.

As discussed above, the sonic velocity (or an estimate of the sonic velocity) of the fluid in the borehole is used to determine the borehole diameter. The sonic velocity varies with fluid density and temperature and is preferably measured while the borehole diameter measurements are made. One simple method for measuring the sonic velocity includes installing a second ultrasonic transducer in the tool body 106 (not shown). The second ultrasonic transducer would have a fixed length acoustic travel path, i.e., a known distance from the transducer to the target. With the distance to the target and travel time known, the sonic velocity can be determined. It will be appreciated that any suitable means for determining the borehole fluid velocity may be use to implement the invention as known in the art. For example, one conventional technique for deriving the fluid sonic velocity uses mud parameters and temperature measurements.

Figure 5:
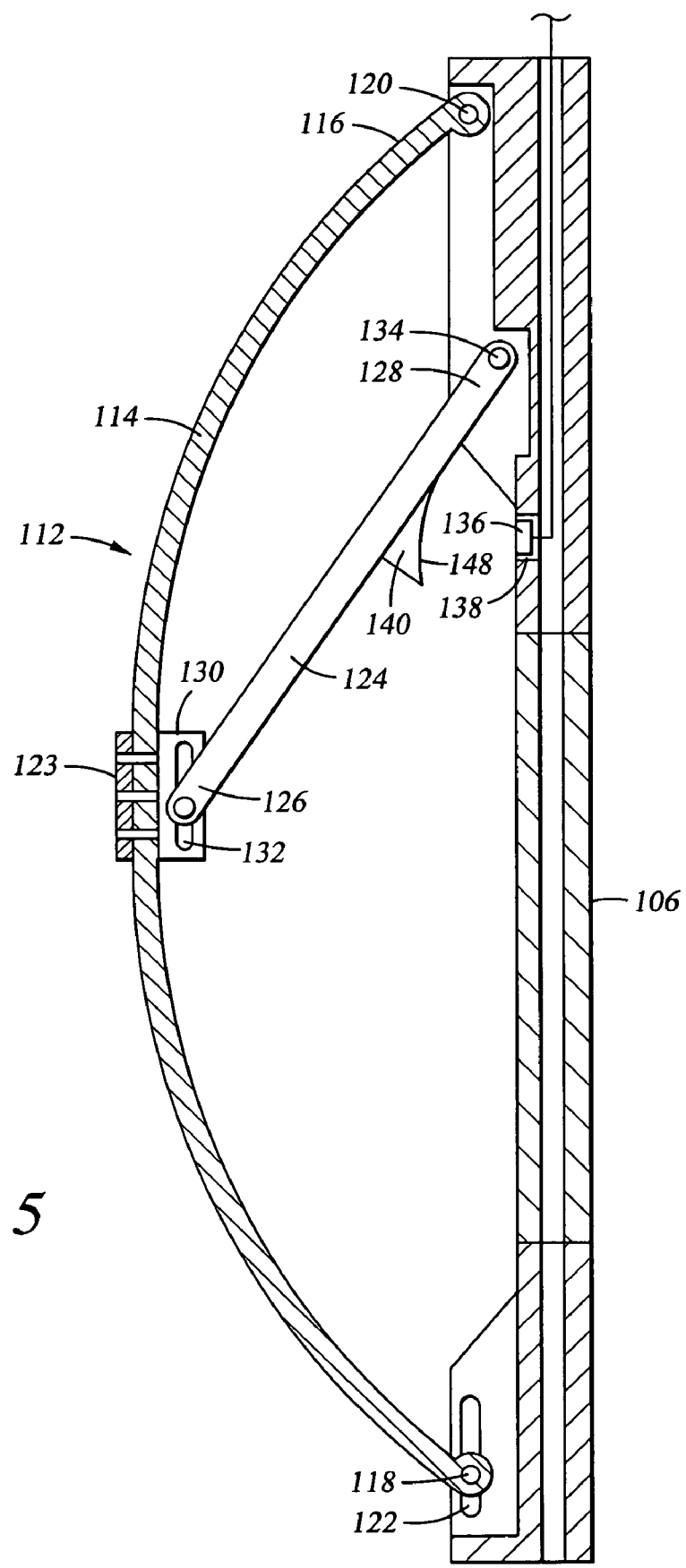
FIG. 5 shows a cross-section of a caliper tool according to another embodiment of the invention.
Figure 6:
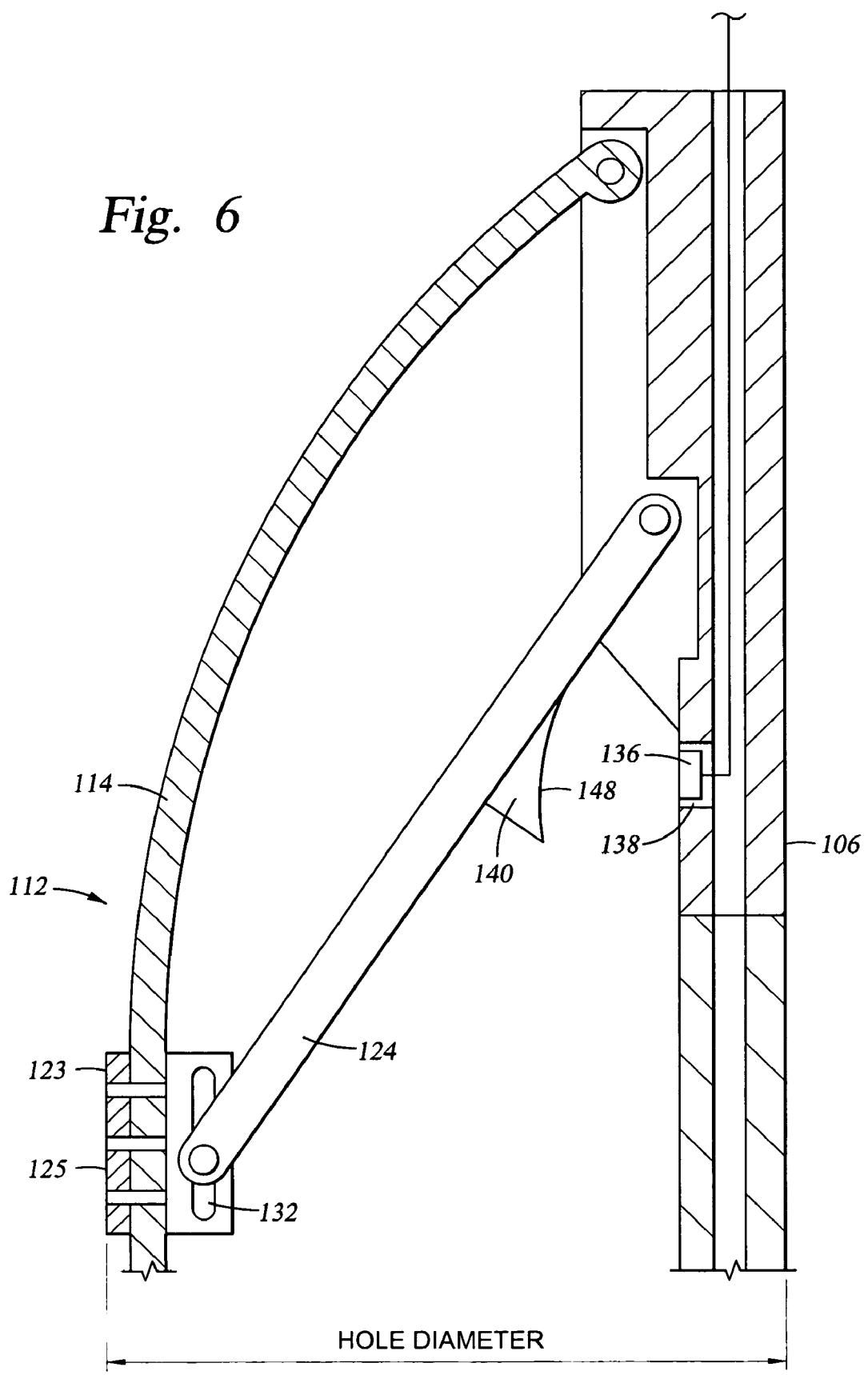
FIG. 6 shows an enlarged view of the caliper tool of FIG. 5.

FIG. 5 shows the tool body 106 and the arm assembly 112 according to another embodiment of the invention. In this embodiment, the arm assembly 112 further includes a rigid follower arm 124 having an end 126 coupled to the bow spring 114 and an end 128 coupled to the tool body 106. A pad 130 attached to the middle portion of the bow spring 114, opposite the pad 123, couples the end 126 of the follower arm 124 to the middle portion of the bow spring 114. The pad 130 includes a slot which cooperates with a pin on the end 126 of the follower arm 124 to form a pin-in-slot joint 132. The joint 132 allows the end 126 to both slide and pivot relative to the bow spring 114. The end 128 of the follower arm 124 is coupled to the tool body 106 via a joint 134, which preferably allows pivoting of the end 128. FIG. 6 shows a more detailed view of this embodiment.

FIG. 5 also shows a pad 140 attached to the follower arm 124. The pad 140 may act as a target for the ultrasonic transducer 136. As in the previous embodiment, when the pad 140 acts as a target for the ultrasonic transducer 136. This embodiment reduces the distance the acoustic wave travels, and subsequently the signal attenuation, compared to the embodiment shown in FIG. 2. A typical transducer's response function half-power point is +/−15 degrees, so it is preferable to maintain the target perpendicular to the axis of the transducer 136. This may be accomplished with a concave surface 148 on the pad 140. Embodiments may be implemented with other configurations to maintain the target perpendicular to the axis of the transducer 136 as known in the art (e.g. by adding a second arm to make a parallelogram mechanism (not shown)). The pad 140 can be positioned on the follower arm 124 such that the distance between the surface 148 and the transducer 136 is within the measurement range of the transducer 136.

Figure 7:
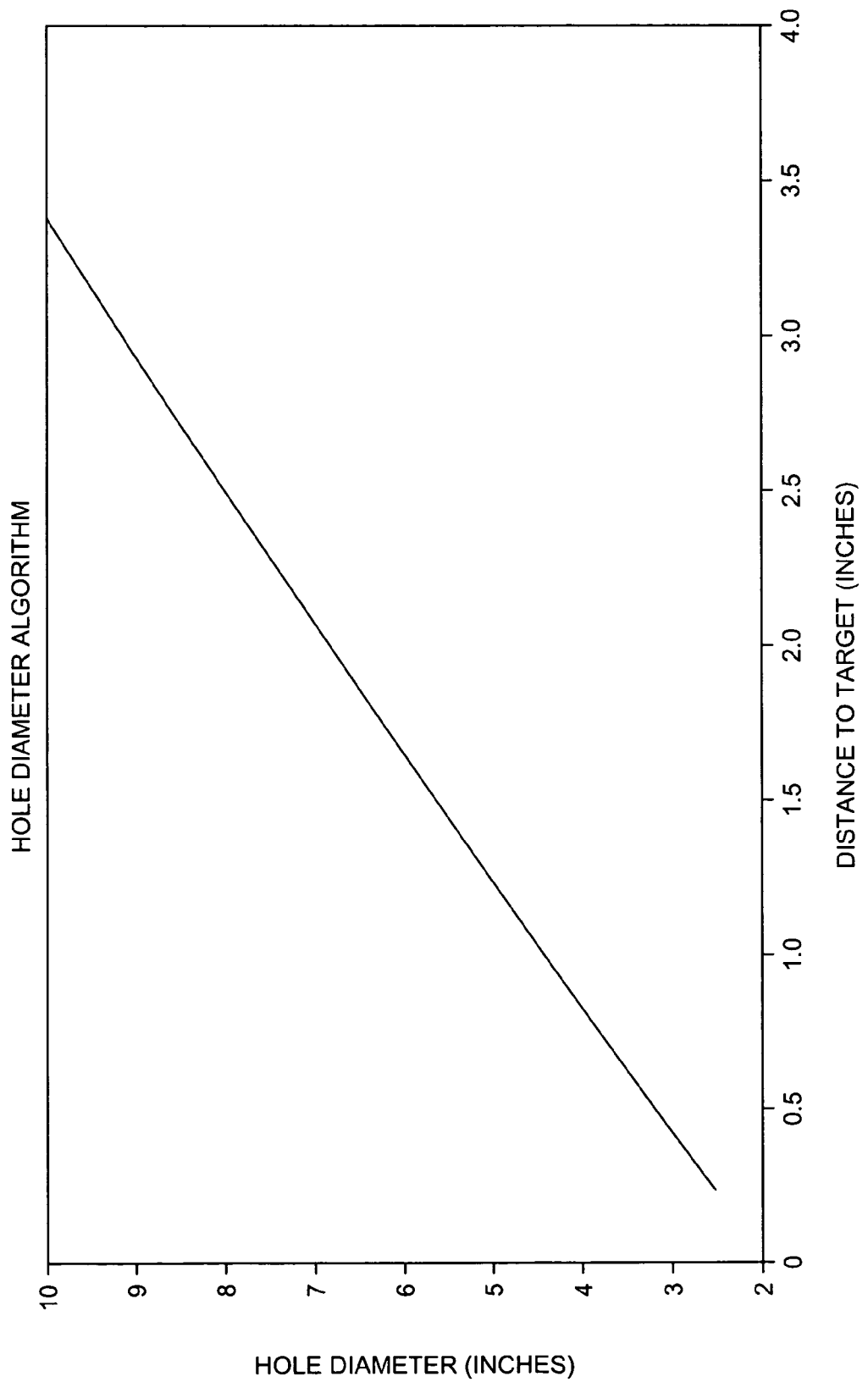
FIG. 7 is a plot illustrating a measurement relationship between a target and borehole diameter in accord with an embodiment of the invention.

In the embodiment described above where the pad 140 surface 148 on the follower arm 124 is used as a target, the travel time measured by the ultrasonic transducer 136 is indicative of the distance between the ultrasonic transducer 136 and the concave surface 148 of pad 140 on the follower arm. FIG. 7 shows the relationship between this measurement and the borehole diameter graphically. The input to the algorithm is the one-way travel time. This is determined by taking half of the two-way time and using the borehole fluid sonic velocity to convert this time to distance. The algorithm may be performed analytically by a suitable processor located in the tool 106 or on the surface as known in the art.

Figure 8:
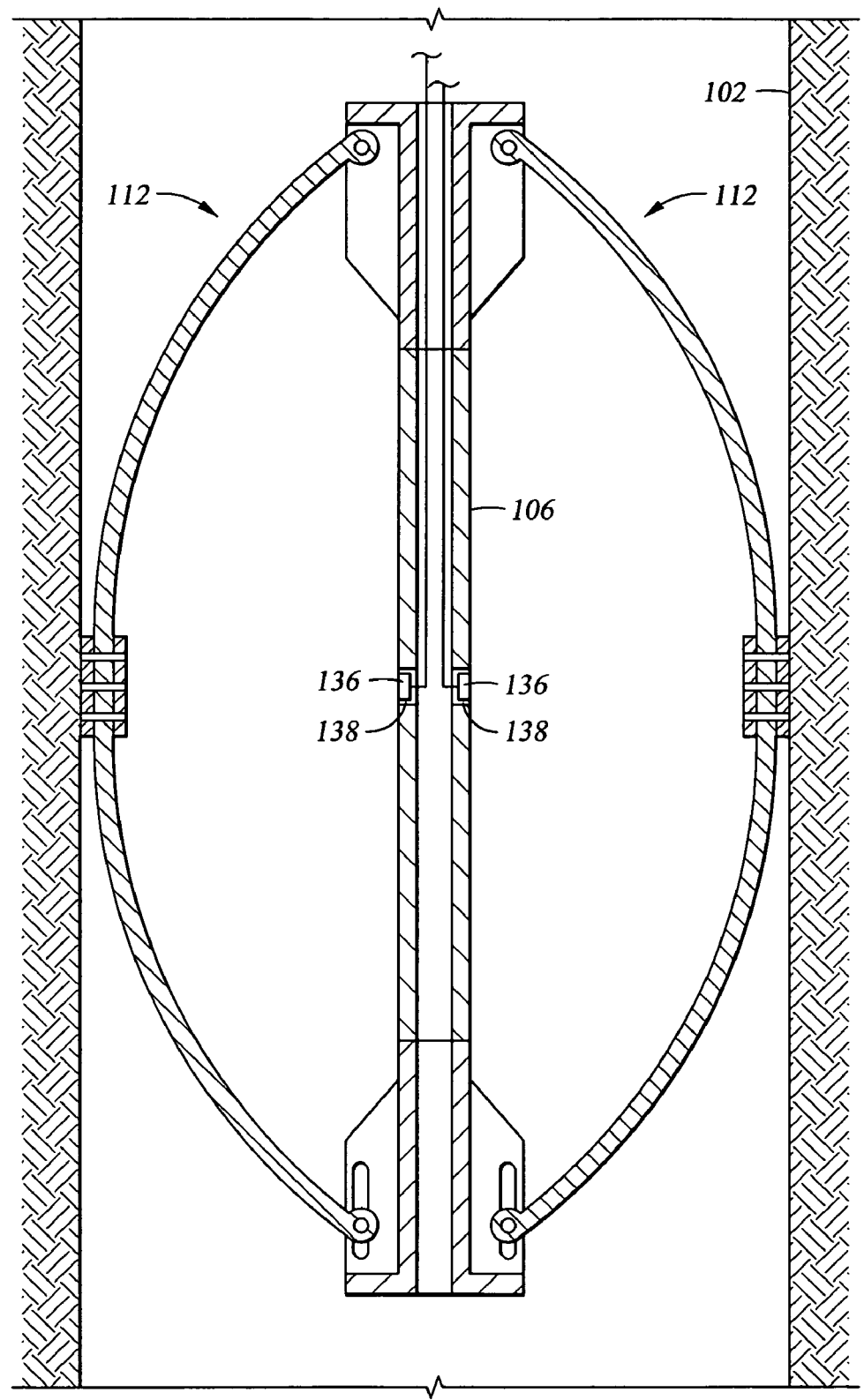
FIG. 8 shows a caliper tool according to another embodiment of the invention.

Various modifications are possible to the embodiments described herein. For example, FIG. 1 shows a single caliper arm assembly 112 coupled to the tool body 106 such that the caliper arm assembly 112 and the tool body 106 both engage or make contact with the borehole wall while making borehole diameter measurements. In an alternate embodiment, as illustrated in FIG. 8, multiple caliper arm assemblies 112 may be coupled to the tool body 106 such that the tool body 106 is centered in the borehole 102 and does not make contact with the borehole wall. In this case, multiple ultrasonic sensors 136 are also mounted in cavities 138 in the tool body 106 to track the motion of the arm assemblies 112. The measurements made by the ultrasonic sensors 136 can be integrated to determine the overall diameter of the borehole. In the embodiment of FIG. 5 where a follower arm 124 is coupled between the bow spring 114 and the tool body 106, the pad 130 or pad 123 may also be adapted to serve as a target for acoustic pulses.

While the invention has been described with respect to a limited number of embodiments, those skilled in the art, having benefit of this disclosure, will appreciate that other embodiments can be devised which do not depart from the scope of the invention as disclosed herein. For example, embodiments of the invention may be implemented to run on a "slick-line" with the measured data stored in memory for retrieval when the tool is brought back to the surface. In such embodiments, the data may be sent to a memory interface that stores the data in non-volatile memory for later retrieval. In real-time applications, some basic processing may be done in the caliper tool as known in the art. The resulting data being sent to a telemetry interface (that could be in a separate downhole instrument) and sent up to a surface acquisition system (e.g. via a wireline).

What is claimed is:

1. A borehole caliper tool, comprising:
   a tool body;
   a bow spring flexibly coupled to the tool body;
   a target coupled to the bow spring; and
   an ultrasonic transducer coupled to the tool body, wherein in operation the ultrasonic transducer transmits an acoustic pulse to the target and receives an echo of the acoustic pulse from the target.

2. The borehole caliper of claim 1, wherein the target is attached to the bow spring.

3. The borehole caliper of claim 1, further comprising a rigid arm coupled to the tool body and the bow spring such that the rigid arm deflects relative to the tool body as the bow spring flexes.

4. The borehole caliper of claim 3, wherein the target is attached to the rigid arm.

5. The borehole caliper tool of claim 3, wherein a pivot joint is formed between the rigid arm and the tool body.

6. The borehole caliper tool of claim 5, wherein a pivot joint is formed between the rigid arm and the bow spring.

7. The borehole caliper tool of claim 6, wherein a sliding joint is formed between the rigid arm and the bow spring.

8. The borehole caliper of claim 1, further comprising means for measuring a sonic velocity of a fluid.

9. The borehole caliper of claim 1, wherein the means for measuring the sonic velocity comprises an ultrasonic transducer with a fixed length acoustic travel path.

10. The borehole caliper of claim 1, wherein the ultrasonic transducer is mounted in a cavity in the tool body.

11. The borehole caliper of claim 1, wherein the target and ultrasonic transducer are positioned such that they are in opposing relation during operation.

12. A borehole caliper tool, comprising:
    a tool body;
    a bow spring disposed on the tool body;
    an ultrasonic transducer coupled to the bow spring; and
    an ultrasonic transducer coupled to the tool body, wherein in operation an acoustic pulse is transmitted from one of said ultrasonic transducers for receipt by the other ultrasonic transducer.

13. The borehole caliper of claim 12, further comprising means for measuring a sonic velocity of a fluid.

14. The borehole caliper of claim 12, wherein the two ultrasonic transducers are positioned such that they are in opposing relation during operation.

15. The borehole caliper of claim 12, wherein the ultrasonic transducer coupled to the tool body is adapted to transmit an acoustic pulse to the ultrasonic transducer coupled to the bow spring.

16. A method for gauging a diameter of a borehole, comprising:
    deploying a borehole caliper tool in the borehole, the borehole caliper tool comprising a tool body, a bow spring flexibly coupled to the tool body, a target coupled to the bow spring, and an ultrasonic transducer coupled to the tool body, the borehole caliper tool being deployed such that the bow spring engages with a surface of the borehole; and
    generating an acoustic pulse using the ultrasonic transducer;
    receiving an echo of the acoustic pulse from the target;
    determining a time elapsed between generating the acoustic pulse and receiving the echo of the acoustic pulse; and
    relating the time elapsed to the diameter of the borehole.

17. The method of claim 16, further comprising estimating a sonic velocity of a fluid in the borehole.

18. A method for gauging a diameter of a borehole, comprising:
    deploying a borehole caliper tool in the borehole, the borehole caliper tool comprising a tool body, a bow spring flexibly coupled to the tool body, an ultrasonic transducer coupled to the bow spring, and an ultrasonic transducer coupled to the tool body, the borehole caliper tool being deployed such that the bow spring engages with a surface of the borehole; and
    generating an acoustic pulse using the ultrasonic transducer coupled to the tool body;
    receiving the acoustic pulse using the ultrasonic transducer coupled to the bow spring;
    determining a time elapsed between generating the acoustic pulse and receiving the acoustic pulse; and
    relating the time elapsed to the diameter of the borehole.

19. The method of claim 18, further comprising estimating a sonic velocity of a fluid in the borehole.

20. A method for gauging a diameter of a borehole, comprising:
    deploying a borehole caliper tool in the borehole, the borehole caliper tool comprising a tool body, a bow spring flexibly coupled to the tool body, an ultrasonic transducer coupled to the bow spring, and an ultrasonic transducer coupled to the tool body, the borehole caliper tool being deployed such that the bow spring engages with a surface of the borehole; and
    generating an acoustic pulse using the ultrasonic transducer coupled to the tool bow spring;
    receiving the acoustic pulse using the ultrasonic transducer coupled to the tool body;
    determining a time elapsed between generating the acoustic pulse and receiving the acoustic pulse; and
    relating the time elapsed to the diameter of the borehole.

21. The method of claim 20, further comprising estimating a sonic velocity of a fluid in the borehole.

* * * * *